(12) United States Patent
Di Cristina

(10) Patent No.: US 11,116,429 B2
(45) Date of Patent: *Sep. 14, 2021

(54) METHOD FOR IN SITU CALIBRATION OF IMPLANTABLE SENSORS

(71) Applicant: Maxim Integrated Products, Inc., San Jose, CA (US)

(72) Inventor: John F. Di Cristina, Acton, MA (US)

(73) Assignee: Maxim Integrated Products, Inc., San Jose, CA (US)

( * ) Notice: Subject to any disclaimer, the term of this patent is extended or adjusted under 35 U.S.C. 154(b) by 627 days.

This patent is subject to a terminal disclaimer.

(21) Appl. No.: 15/927,961

(22) Filed: Mar. 21, 2018

(65) Prior Publication Data
US 2019/0090792 A1    Mar. 28, 2019

Related U.S. Application Data

(63) Continuation of application No. 14/805,330, filed on Jul. 21, 2015, now Pat. No. 9,949,673.

(60) Provisional application No. 62/042,122, filed on Aug. 26, 2014.

(51) Int. Cl.
*A61B 5/1495* (2006.01)
*A61B 5/145* (2006.01)
*A61B 5/1473* (2006.01)

(52) U.S. Cl.
CPC ........ *A61B 5/14532* (2013.01); *A61B 5/1473* (2013.01); *A61B 5/1495* (2013.01); *A61B 2560/0223* (2013.01)

(58) Field of Classification Search
CPC .............. A61B 5/1455; A61B 5/14551; A61B 5/14552; A61B 5/14532; A61B 5/1473; A61B 5/1495; A61B 2560/0223
See application file for complete search history.

(56) References Cited

U.S. PATENT DOCUMENTS

| | | | |
|---|---|---|---|
| 5,237,993 A | 8/1993 | Skrabal | |
| 6,770,030 B1 * | 8/2004 | Schaupp | ............ A61B 5/14532 600/309 |
| 8,140,140 B2 | 3/2012 | Sterling et al. | |
| 2004/0191848 A1 | 9/2004 | Hoss et al. | |
| 2004/0220552 A1 | 11/2004 | Heruth et al. | |
| 2005/0277912 A1 | 12/2005 | John | |
| 2006/0058602 A1 | 3/2006 | Kwiatkowski et al. | |
| 2010/0094114 A1 | 4/2010 | Robinson et al. | |
| 2012/0065482 A1 | 3/2012 | Robinson et al. | |
| 2012/0123230 A1 | 5/2012 | Brown et al. | |

(Continued)

FOREIGN PATENT DOCUMENTS

WO    2006/103061 A1    10/2006

*Primary Examiner* — Chu Chuan Liu
(74) *Attorney, Agent, or Firm* — TIPS Group

(57) ABSTRACT

A subcutaneous sensor system includes a sensor, a plurality of reservoirs, a plurality of pumps, a mixer provided with a plurality of mixer inlets and a mixer outlet, and a controller having an input coupled to the sensor output and a plurality of control outputs coupled to the plurality of pumps and the mixer. In certain embodiments, the system further includes an enclosure for the reservoirs, the pumps, the mixer and the controller, e.g. in the form of a skin patch or in the form of an implantable enclosure. In certain embodiments, the sensor is external to the enclosure and implanted beneath the skin tissue.

17 Claims, 5 Drawing Sheets

(56) References Cited

U.S. PATENT DOCUMENTS

2013/0328572 A1 12/2013 Wang et al.
2014/0371553 A1 12/2014 Winkelman
2016/0073940 A1 3/2016 Winkelman

* cited by examiner

METHOD FOR IN SITU CALIBRATION OF IMPLANTABLE SENSORS

CROSS REFERENCE TO RELATED APPLICATION(S)

This application is a continuation of U.S. Ser. No. 14/805,330, filed Jul. 21, 2015, which claims the benefit of U.S. Ser. No. 62/042,122, filed Aug. 26, 2014, both of which are incorporated herein by reference.

BACKGROUND

Clinical chemistry enables the analysis of biological fluids for diagnosing, monitoring, and/or treating the medical condition of a patient. By way of example, determining the level of analytes such as glucose, lactate, creatinine, electrolytes, and oxygen can be vitally important for monitoring and/or maintaining a patient's health and treatment. Moreover, a patient's reaction to the administration of certain substances (e.g. glucose) can be used in diagnostic stress-tests. Similarly, by monitoring the level of xenobiotics such as insulin or drugs and their metabolites, physicians can diagnose kidney and liver disorders or select appropriate dosing in drug treatment. For example, monitoring the pharmacokinetics of a drug under treatment conditions in a particular patient can allow individualized optimization of the treatment schedule and help avoid potentially serious drug-drug interactions.

Although centralized clinical laboratories can provide a wide array of assays for accurately determining the presence and/or concentration of various analytes, clinical laboratories typically require that a sample (e.g., blood) be obtained from a patient, shipped to a laboratory, and processed and tested prior to the results being communicated back to the patient's physician. While recent advances in point-of-care (POC) diagnostics have enabled some laboratory tests to be quickly performed at the patient's bedside, these assays are not without drawbacks as the accuracy and precision of POC instruments often suffer relative to their central lab counterparts.

By way of example, blood glucose has been the most frequently performed clinical chemistry laboratory test for the past several decades based, in part, on it serving as the primary indication for diabetes detection and monitoring of therapy. Over the last years, however, self-testing of blood glucose has become increasingly common with the advent of POC glucometers that allow an individual to lance their fingertip, expel a drop of blood onto a test strip that can be inserted into the glucometer, and obtain an almost immediate measurement of his or her blood glucose level.

Despite the frequency of sampling (e.g., at 15-, 30-, 60-, or 240-minute intervals as specified by protocols), monitoring provided by glucometers and other analyte monitors is nonetheless discontinuous, providing a snapshot of analyte levels in the blood at the moment that the sample was obtained. Accordingly, systems have been developed to continuously measure the concentration of analytes in subcutaneous interstitial fluid, for example, since the concentration of certain analytes (e.g., glucose) is highly correlated between these two fluid compartments (Bantle, et al., J. Lab. Clin. Med. 1997; 130: 436-441), incorporated herein by reference. By way of example, sensors for continuous monitoring of certain analytes (e.g., glucose) in interstitial fluid are known in the art. U.S. Pat. No. 6,579,690 of Bonnecaze et al. and U.S. Application Pub. No. 2008/0027296 of Hadvary et al., both of which are incorporated herein by reference, provide continuous analyte monitoring systems that may enable better glycemic control through continuous, real-time monitoring of a patient's interstitial fluid glucose levels. Some such systems, for example, employ an electrochemical sensor that can be implanted within subcutaneous tissue and remain in contact with the interstitial fluid for an extended time (e.g. several hours to a week or more). The voltage output of the sensor can be transmitted to a data processing unit (e.g. a microprocessor, a microcontroller, etc.) for converting the sensor output to a blood glucose equivalent value.

Like POC glucometers and other POC analyte measurement systems, implantable analyte monitoring systems can suffer from diminished accuracy and precision relative to their clinical laboratory counterparts. Moreover, the long-term implantation of these monitors can diminish the reliability of the data transmitted by the sensor(s) as other components in body fluids (e.g., proteins) can contaminate the sensors and cause inaccurate readings. As a result, current continuous analyte monitoring systems generally require frequent calibration or confirmation using other more invasive and/or less convenient techniques. By way of example, prior to treating a patient in whom their continuous blood glucose monitor indicates a low blood glucose level, a medical caretaker is generally required to confirm the levels using the standard-of-care POC glucometers. Likewise, diabetics using implantable, continuous glucose monitors are nonetheless prompted to provide a finger stick measurement for regular calibration of their monitors and/or prior to treatment. Accordingly, there remains a need for improved accuracy and reliability of implantable, continuous analyte monitoring systems, such as the continuous glucose monitor (CGM).

A CGM typically takes the form of a patch which is applied to the skin or implanted under the skin. Typically, the electrochemical sensor associated with the CGM patch is either implanted or inserted inside the human body and is therefore subject to a "foreign body response" where the body tries to render the sensor inert. This response changes the performance of the sensor as well as aging of the sensor may also change the performance. It is therefore desirable to have an in situ method for recalibrating sensors as their performance changes with time.

Systems, devices and methods for in situ calibration of implantable sensors are described in International Application No. PCT/US2012/070025 of Winkelman (published as WO 2013/090882 A1) incorporated herein by reference. In one aspect, Winkelman describes a system for monitoring the concentration of an analyte including a sensor configured to be implanted at an implant site in a patient's skin, the sensor configured to sense an analyte present in a biological fluid at the implant site. The described system can additionally include a reservoir, which contains a calibration fluid having a known concentration of the analyte, and a conduit for delivering the calibration fluid from the reservoir to the implant site, to allow for the calibration of the system.

While Winkelman provides the advantage of being an in situ calibration solution, it is limited by its single-point calibration methodology. With Winkelman, a "calibration fluid", e.g. a control solution of a known value such as 100 mg/dL, is pumped from a reservoir into the interstitial tissue proximate to the sensor. The known value may be far from the value that the sensor was measuring, potentially causing a significant calibration error. Also, Winkelman only measures at a single point, such that both the gain and offset of the transfer function for the linear range of the sensor may be skewed. Still further, the method disclosed by Winkelman is limited in application due to the use of a single, fixed reservoir of calibration fluid.

These and other limitations of the prior art will become apparent to those of skill in the art upon a reading of the following descriptions and a study of the several figures of the drawing.

SUMMARY

In non-limiting examples, systems and processes are provided to calibrate an in situ electrochemical sensor with a control ("calibration") solution that can be programmed to continuous values in the range of the sensor's linear measurement range. The systems and processes are described with reference to example continuous glucose monitors but can also be used for an electrochemical sensor measuring chemicals other than glucose in interstitial fluid or blood. The example programmable control solution can provide a single point calibration that can quickly return to measuring glucose and/or can provide a two point calibration resulting in a more accurate glucose reading compared to a single point calibration. Furthermore, the example systems and processes described herein can provide a safety check on the sensor operation, or perform a cleaning of the sensor, to ensure proper operation.

In an embodiment, set forth by way of example but not limitation, a subcutaneous sensor system or device with multiple reservoirs for calibrating solutions includes a sensor having a sensor output; a plurality of reservoirs provided with a corresponding plurality of reservoir outlets; a plurality of pumps provided with a corresponding plurality of pump inlets and a corresponding plurality of pump outlets, wherein the plurality of pump inlets are coupled to the plurality of reservoir outlets; a mixer provided with a plurality of mixer inlets and a mixer outlet, wherein the plurality of mixer inlets are coupled to the plurality of pump outlets; and a controller having an input coupled to the sensor output and a plurality of control outputs coupled to the plurality of pumps and the mixer. In certain embodiments, the system further includes an enclosure for the reservoirs, the pumps, the mixer and the controller, e.g. in the form of s skin patch or in the form of an implantable enclosure. In certain embodiments, the sensor is external to the enclosure and implanted beneath the skin tissue.

In certain non-limiting examples the controller includes a microcontroller unit (MCU) including digital memory, a sensor analog front end (AFE) coupling the MCU to the sensor with a conductor at least partially enclosed within a tube connected to the mixer output, a data interface coupled to the MCU, and an auto-calculation (Autocal) controller coupling the MCU to the plurality of pumps and to the mixer.

In certain example embodiments, the system is provided with a plurality of reservoirs filled with control ("calibration") solutions of different values. For example, the system can include a first reservoir of the plurality of reservoirs contains a first calibration solution and a second reservoir of the plurality of reservoirs contains a second calibration solution different from the first calibration solution. For example, the first calibration solution is chosen to be proximate a first end of a linear operating region of the sensor and the second calibration solution is chosen to be proximate a second end of the linear operating region of the sensor. In certain example embodiments, the first calibration solution and the second calibration solution can be mixed in the mixer to provide a third calibration solution that is intermediate to the first calibration solution and the second calibration solution. In other example embodiments, the system includes a third reservoir for a cleaning solution. In certain embodiments, the mixer includes one or more mixing valves, and the controller is, in part or in whole, provided as an integrated circuit.

In an embodiment, set forth by way of example and not limitation, a method for operating a subcutaneous sensor system with multiple reservoirs for calibrating solutions includes: (a) detecting the presence of calibration-triggering event with a microcontroller; (b) measuring an initial value of the interstitial tissue of a patient with a subcutaneous sensor; (c) bathing the sensor with a first calibration solution having a different value than the initial value, the first calibration solution being provided from at least one of a plurality of reservoirs; (d) measuring a first calibration value from the sensor that is associated with the first calibration solution; (e) bathing the sensor with a second calibration solution having about the same value as the initial value, the second calibration solution being provided by at least one of the plurality of reservoirs; (f) calculating the gain (m) and offset (b) for the sensor, whereby the transfer function f(x) for the sensor comprises $y=f(x)=mx+b$; and (g) using the transfer function to measure a calibrated sensor value of the sensor. In the case of a CGM, the initial value can be for example, the initial glucose value of the interstitial fluid of a patient.

An advantage of certain example embodiments is that the need for diabetics to perform finger stick blood glucose measurements multiple times daily to calibrate their CGM patches is eliminated.

A further advantage of certain example embodiments is that a CGM can return to measuring glucose in the interstitial fluid faster than in the prior art after performing a single point (offset) calibration.

A still further advantage of certain example embodiments is that a multi-point measurement can be made to perform a two-point (gain and offset) calibration.

Another advantage of certain example embodiments is that a safety check of the sensor's operation can be performed.

Yet another advantage of certain example embodiments is that a cleaning of the sensor can be accomplished with a specialized cleaning fluid.

These and other embodiments, features and advantages will become apparent to those of skill in the art upon a reading of the following descriptions and a study of the several figures of the drawing.

BRIEF DESCRIPTION OF THE DRAWINGS

Several example embodiments will now be described with reference to the drawings, wherein like components are provided with like reference numerals. The example embodiments are intended to illustrate, but not to limit, the invention. The drawings include the following figures.

DETAILED DESCRIPTION OF EXAMPLE EMBODIMENTS

Figure 1:
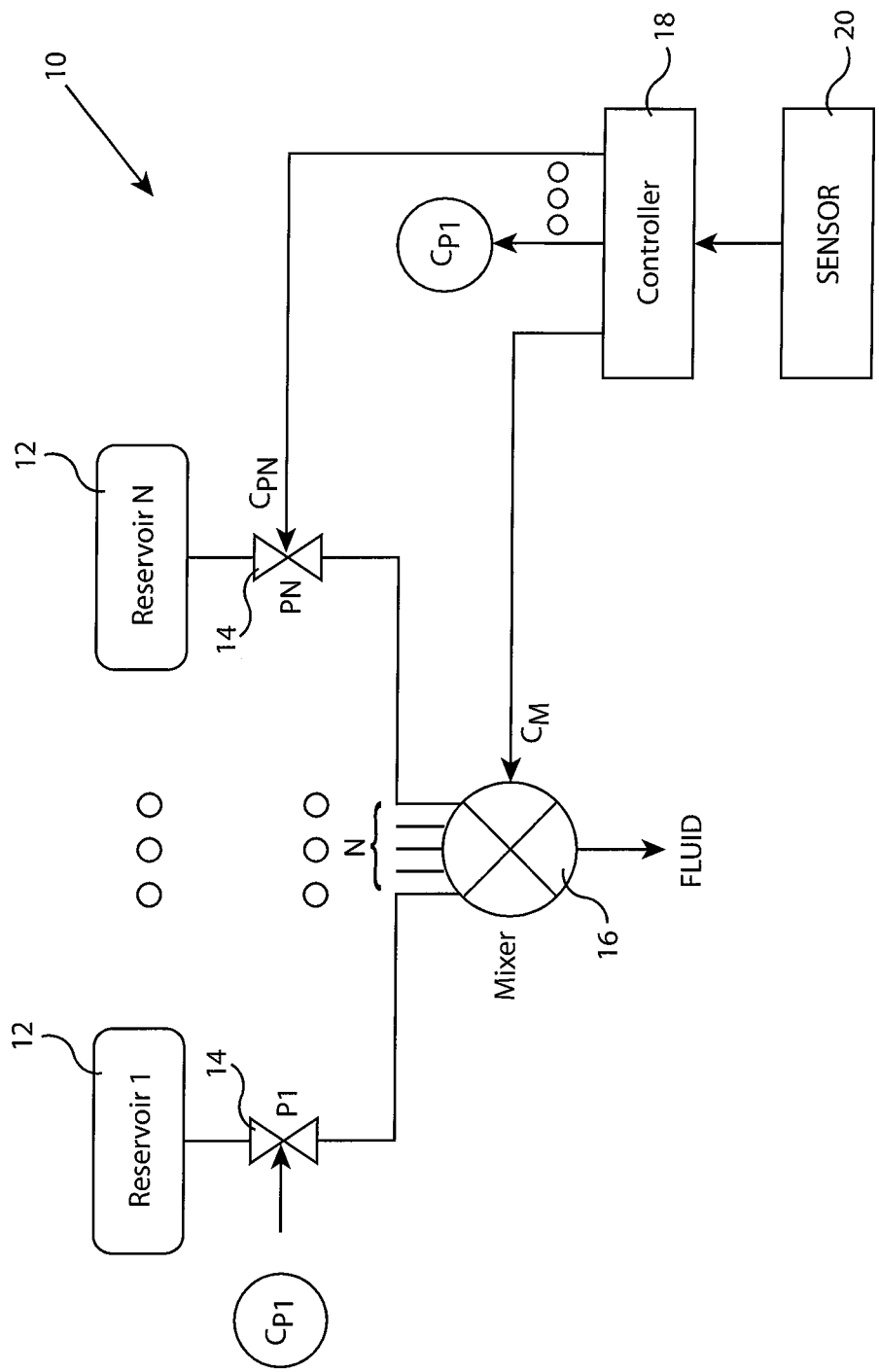
FIG. 1 is a block diagram, set forth by way of example and not limitation, of a subcutaneous sensor system with multiple reservoirs for calibrating solutions.

FIG. 1 is a block diagram, set forth by way of example and not limitation, of a subcutaneous sensor system 10 with a plurality of reservoirs 12 for solutions. Sensor system 10 also includes a plurality of pumps 14, a mixer 16, a controller 18 and a subcutaneous sensor 20. In this non-limiting example, there are N reservoirs 12, at least two of which include calibrating solutions of different values. In an embodiment, at least one of the reservoirs includes a cleaning solution. In this non-limiting example, there are N pumps 14 (labelled P1-PN) to couple N inlets of mixer 16 to N outlets of reservoirs 12. The pumps P1-PN are controlled by control lines $C_{P1}$-$C_{PN}$ coupled to outputs of the controller 18. Mixer 16 is controlled by control line $C_M$ coupled to an output of the controller. It should be noted that mixer 16 can be a single mixing valve or a plurality of mixing valves. Sensor 20 is coupled to an input of controller 18.

Figure 2:
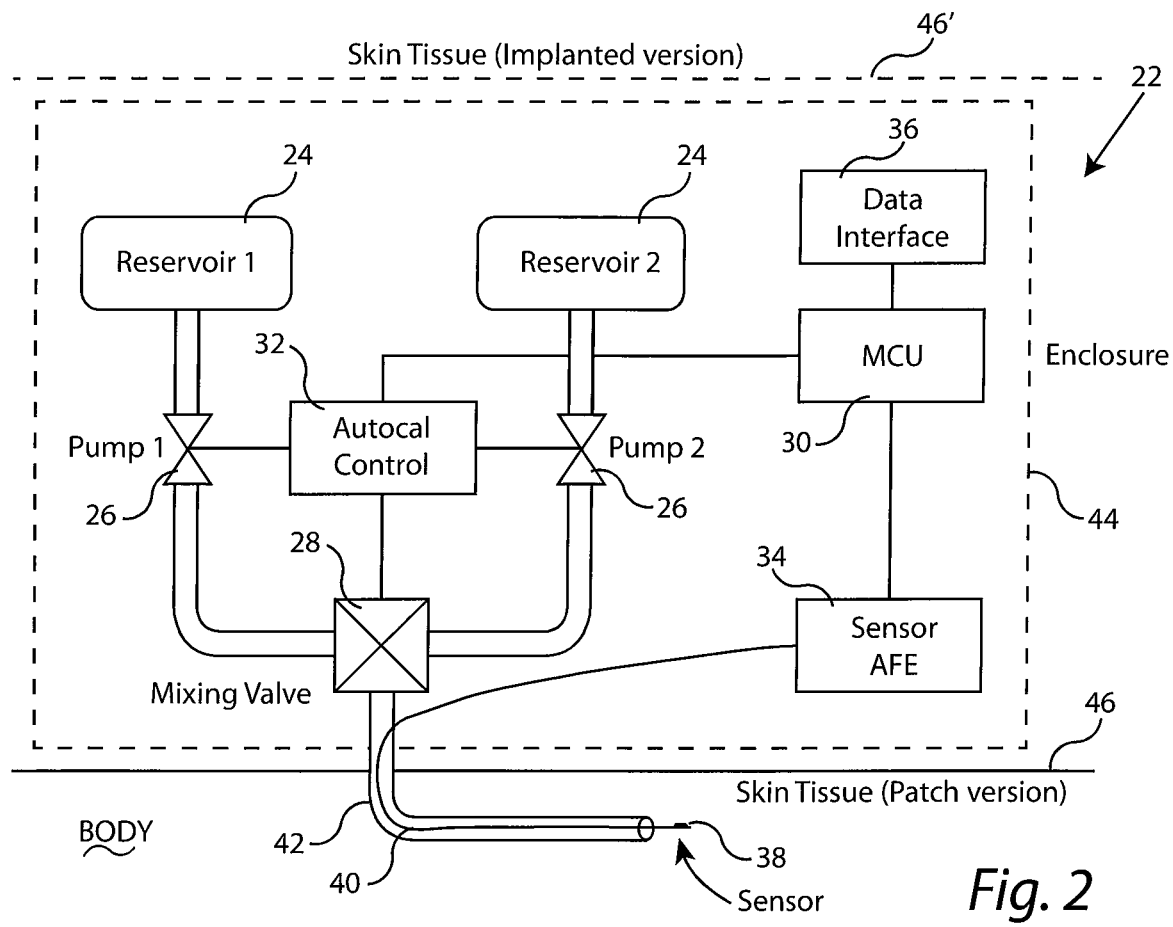
FIG. 2 is a block diagram, set forth by way of example and not limitation, of a subcutaneous sensor system with two reservoirs suitable for use as a continuous glucose monitor (CGM)

FIG. 2 is a block diagram, set forth by way of example and not limitation, of a subcutaneous sensor system 22 with two reservoirs 24 suitable for use as a continuous glucose monitor (CGM). In this non-limiting example, two pumps 26 couple outlets of the reservoirs 24 to a mixing valve 28. Also in this example embodiment, controller components are distributed among a microcontroller unit 30, an Autocalibration (Autocal) Control 32, a sensor analog front end (Sensor AFE) 34 and Data Interface 36. A subcutaneous sensor 38 is coupled to an input of the Sensor AFE by a conductor 40 which, in this non-limiting example, is at least partially disposed within a tube 42 coupled to an outlet of mixing valve 28.

In this non-limiting example, the reservoirs 24, pumps 26, mixing valve 28 MCU 30, Autocal Control 32, Sensor AFE 34 and Data Interface 36 are disposed within an enclosure 44. In one example embodiment, the enclosure 44 is a skin patch which sits on top of skin tissue 46, and in another example embodiment the enclosure is implanted within the body so as to be beneath skin tissue 46'. The tube 42, conductor 40 and sensor 38 extend from the enclosure into the body of a patient.

Figure 3:
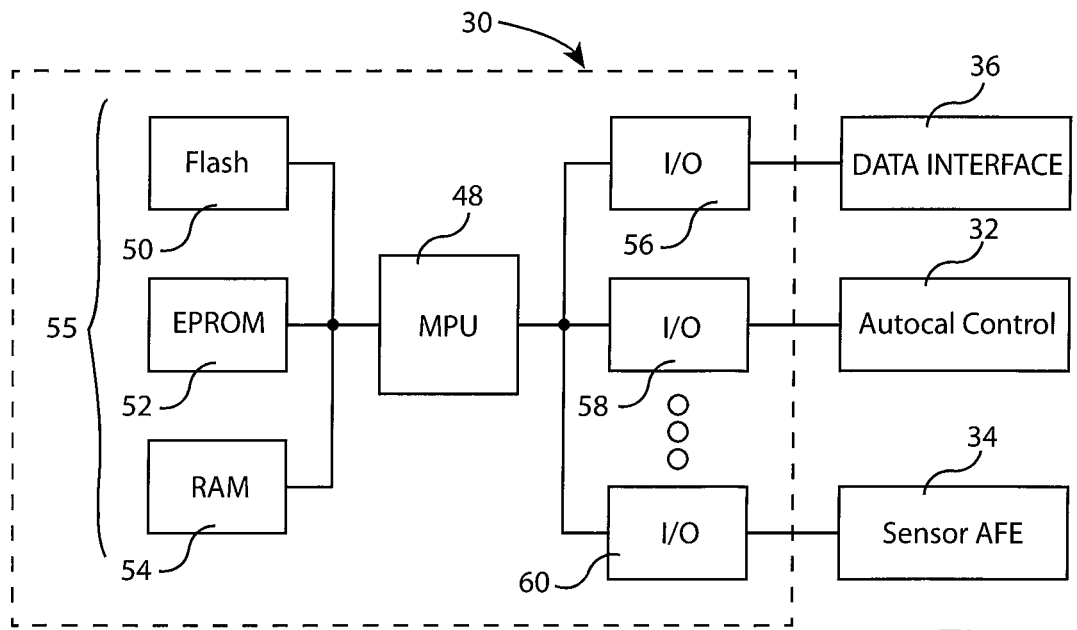
FIG. 3 is a block diagram, set forth by way of example and not limitation, of a microcontroller unit (MCU) of FIG. 2.

FIG. 3 is a block diagram, set forth by way of example and not limitation, of a microcontroller unit (MCU) 30 of FIG. 2. The MCU 30, in this non-limiting example, includes a microprocessor unit (MPU) 48, flash memory 50, electrically programmable read-only memory (EPROM) 52, random access memory (RAM) 58, and input/output (I/O) ports 56, 58 and 60. Collectively, flash memory 50, EPROM 52 and RAM 54 comprise digital memory 55 (a/k/a non-transitory computer readable media) that can be accessed by MPU 48. In this non-limiting example, I/O 56, 58 and 60 couple Data Interface 36, Autocal Control 32 and Sensor AFE 34, respectively, to MPU 48.

Figure 4:
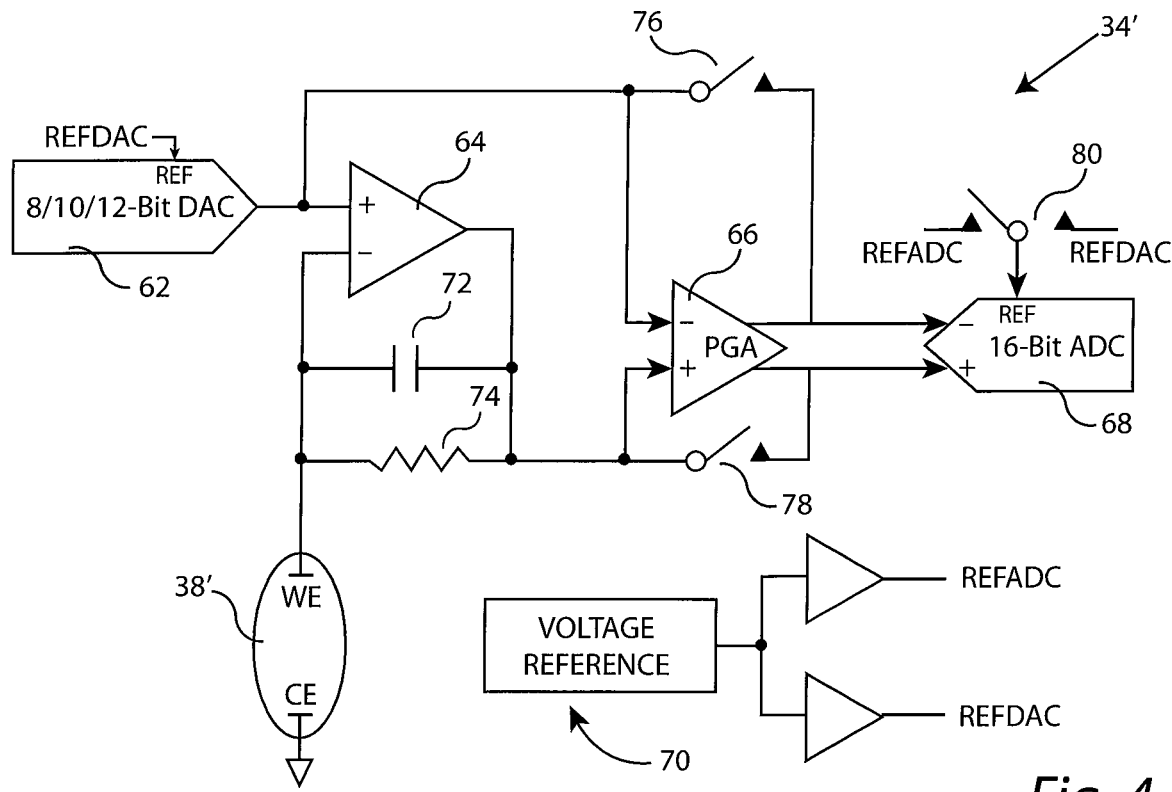
FIG. 4 is a block diagram, set forth by way of example and not limitation, of a sensor analog front end (AFE) for the subcutaneous sensor system of FIG. 2.

FIG. 4 is a block diagram, set forth by way of example and not limitation, of a first sensor analog front end (AFE) 34' for a subcutaneous sensor 38'. In this non-limiting example, AFE 34' includes a digital-to-analog converter (DAC) 62, an operational amplifier 64, a differential programmable gain amplifier (PGA) 66, and an analog-to-digital converter (ADC) 68. The AFE 34' also includes a reference voltage generator 70 producing a reference voltage REFADC for the ADC and a reference voltage REFDAC for the DAC. A negative feedback network comprising a capacitor 72 and resistor 74 is provided for operational amplifier 64, and switches 76 and 78 selectively either engage or bypass the PGA 66. A single-pole double-throw (SPDT) switch 80 selectively couples either REFADC or REFDAC to the reference input of ADC 68. Sensor 38' is coupled between the negative input to operational amplifier 64 and ground. In this non-limiting example, sensor 38' is a two-terminal, self-biased electrochemical sensor.

Figure 5:
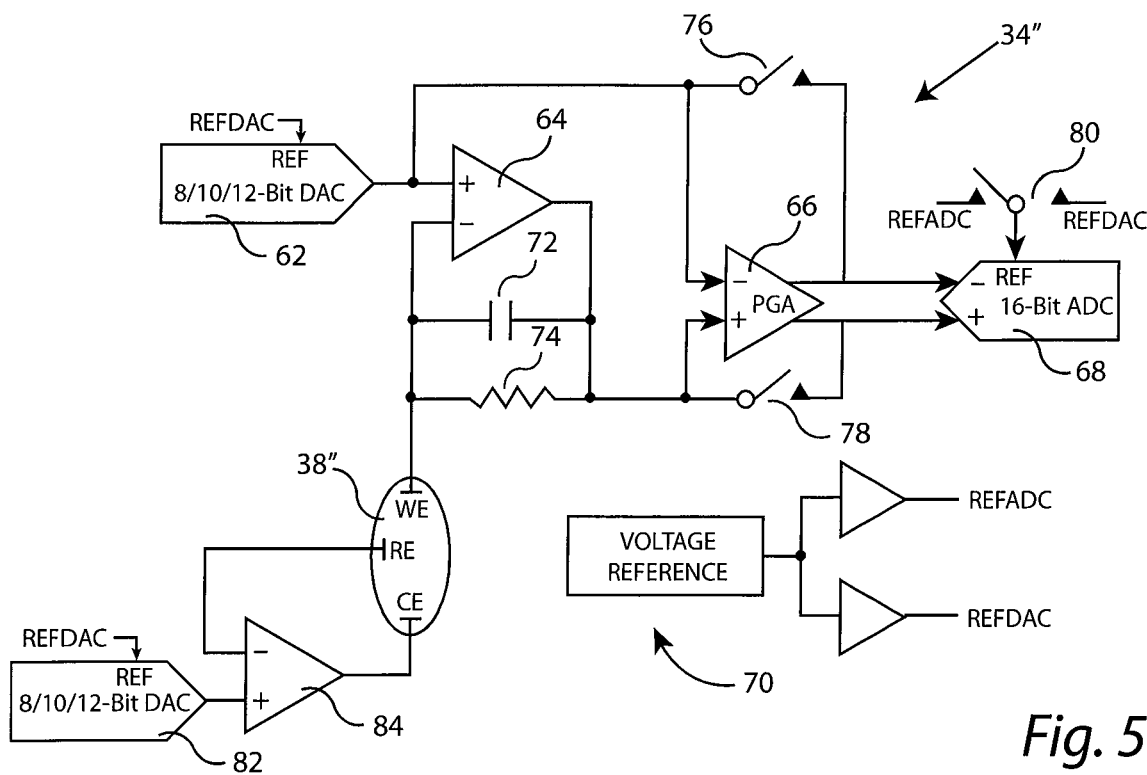
FIG. 5 is a block diagram, set forth by way of example and not limitation, of another sensor analog front end (AFE) for the subcutaneous sensor system of FIG. 2.

FIG. 5 is a block diagram, set forth by way of example and not limitation, of a second sensor analog front end (AFE) 34" for the subcutaneous sensor 38". AFE 34" is substantially similar to AFE 34', where like reference numbers refer to like components, but with the addition of a DAC 82 and an operational amplifier 84 coupled to sensor 38". In this non-limiting example, sensor 38" is a three-terminal, counter configuration electrochemical sensor.

Figure 6:
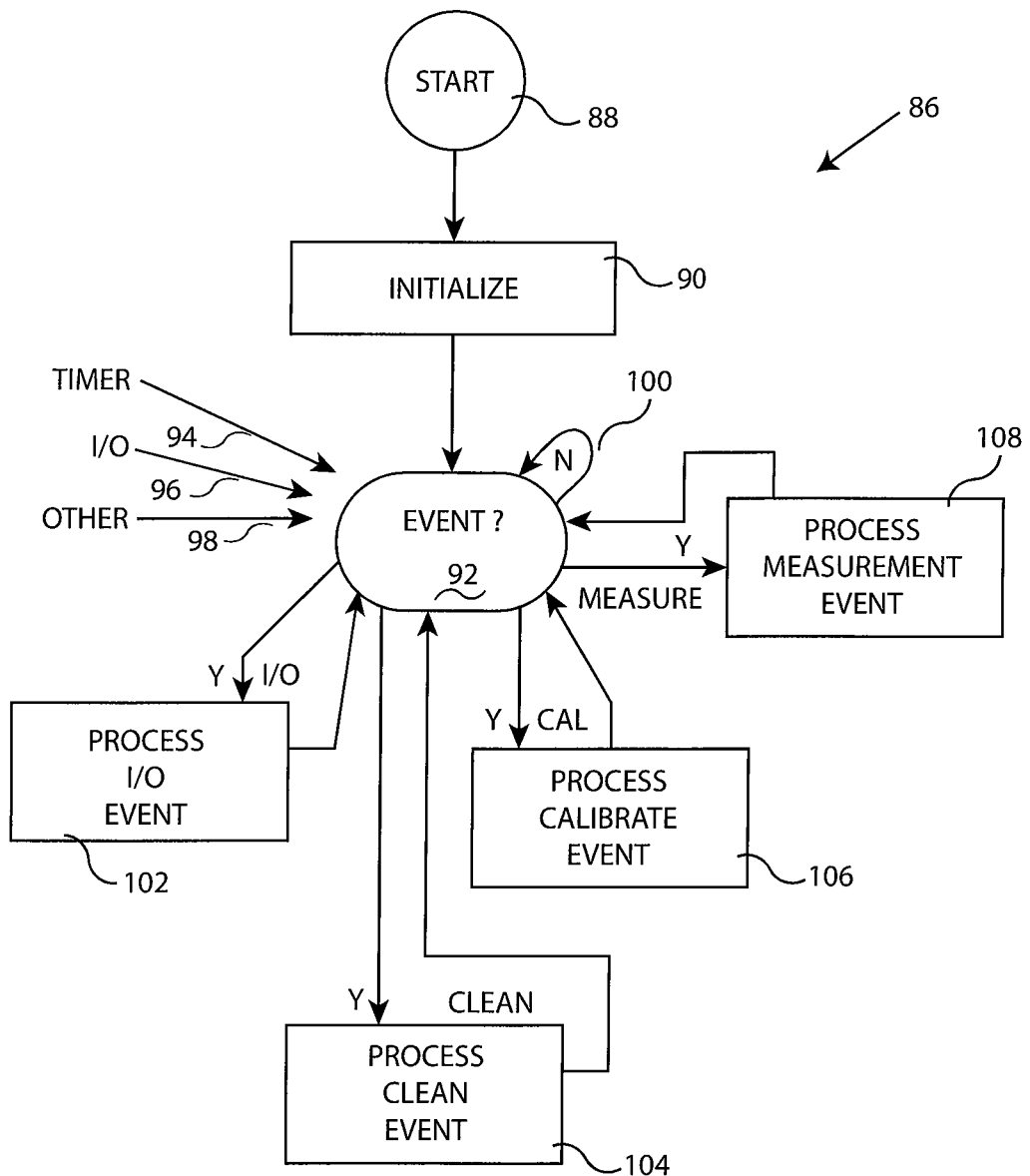
FIG. 6 is a flow diagram, set forth by way of example and not limitation, of an example process stored as code segments in memory and executing on the processor of the microcontroller unit (MCU) of FIG. 3.

FIG. 6 is a flow diagram, set forth by way of example and not limitation, of an example process 86, which can be stored as code segments in memory 55 to be executed by MCU 48 of FIG. 3. Process 86 begins, typically upon power-up, at 88 and, in an operation, the system initializes. Next, in an event loop 92, various inputs such as a timer 94, I/O 96 and Other 98 are monitored for events (which can be in the form of interrupts to the MCU 48). If there are no events to process, the event loop 92 continues to idle as indicated at 100.

If an I/O event is detected by event loop 92 it is processed by operation 102, after which time process control returns to the event loop 92. Similarly, clean events, calibrate events, and measurement events are processed by operations 104, 106 and 108, respectively. Several of the events can be triggered by a timer input 94. For example, measurements events can be processed by operation 108 on a regular, timed basis. Calibrate events can similarly be performed on a regular basis, or just after startup. I/O events may be externally triggered by an operator, and clean events may be initiated when the system fails to properly calibrate. Other events and triggers, as well as other event-driven processes, will be apparent to those of skill in the art.

Figure 7:
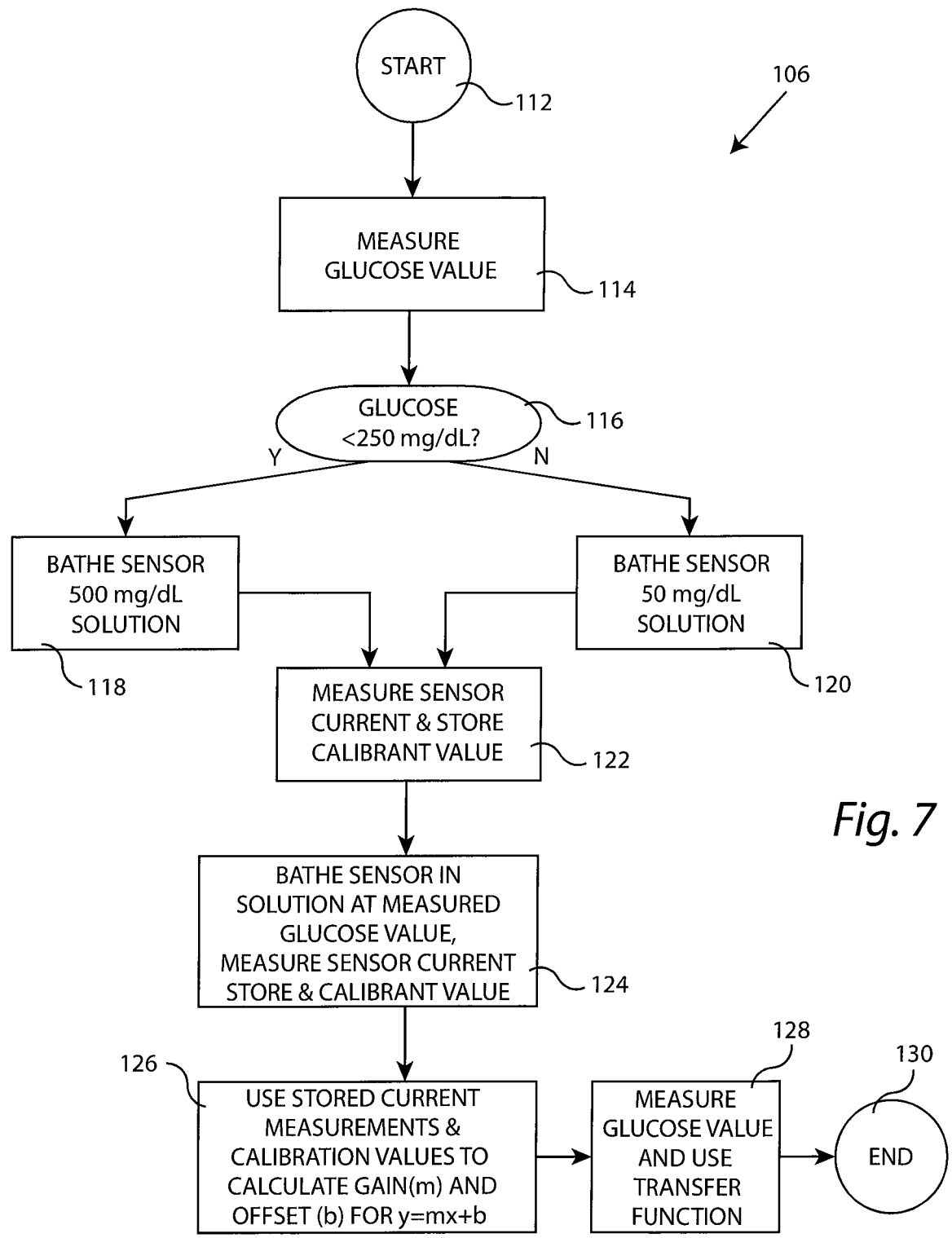
FIG. 7 is a flow diagram, set forth by way of example and not limitation, of an example Process Calibrate Event process of FIG. 6.

FIG. 7 is a flow diagram, set forth by way of example and not limitation, of an example Process Calibrate Event process 106 of FIG. 6. This example process, which is described with reference to the monitoring of glucose levels in, for example, a continuous glucose monitor (CGM), begins at 112 and, in an operation 114, the current glucose value is measured in an operation 114. Next, it is determined if the glucose value is less than 250 mg/dL. If so, the sensor is bathed in a 500 mg/dL calibration solution from one of the reservoirs. If not, the sensor is bathed in a 50 mg/dL calibration solution from another one of the reservoirs. Next, in an operation 122, the sensor current is measured and stored along with the selected calibration solution value. In an operation 124, the sensor is then bathed in a mixed calibration solution derived from the two reservoirs at the measures glucose value of operation 114. Operation 126 uses the stored current measurements and the calibration values to calculate gain (m) and offset (b) for the transfer function f(x) for the linear range of the sensor as given by:

$$y=f(x)=mx+b \qquad \text{Equation 1}$$

The transfer function can then be used to transform the electrical current value "x" measured by the sensor to calibrated glucose values "y" in an operation 128. The process 106 is then completed at 130.

It will be appreciated that, in the example embodiments set forth above, that a calibration solution can be programmed over a range of 50 to 500 mg/dL depending on what value the sensor is reading and desired action to be taken. During a single point calibration, the control solution can bathe the sensor with the value that the sensor is currently measuring so that the sensor doesn't deviate significantly from its current value. In general, the time constant on these sensors is large, so if they are calibrated close to the current value the time to return to measuring glucose in the interstitial fluid will be significantly faster. Also, in certain example embodiments, a two-point calibration can be performed because of the ability to program the calibration solution such that it can sequentially bathe the sensor at a first value such as 50 mg/dL, and then in a second value closer to the measured value, such as 200 mg/dL. This results in transfer function calibration that provides more accurate glucose measurements in the interstitial fluid. Also, example embodiments can perform a safety check on the sensor operation by intentionally bathing the sensor with a control solution that is intentionally far from the current value to see how the sensor responds to this change in glucose, or the sensor can be bathed in a cleaning solution provided by an additional reservoir.

The apparatus block diagram in FIG. 2 illustrates the system components for the example of a CGM. More particularly, Reservoir 1 and Reservoir 2, of this non-limiting example, contain a control solution used to calibrate the sensor 38. One reservoir has a control solution at the low end of the linear measurement range, such as 50 mg/dL, and the other reservoir has a control solution at the high end of the linear measurement range, such as 500 mg/dL. Pump 1 and Pump 2 pump a programmable volume of control solution from each reservoir to be mixed in mixing valve 28 to create a control ("calibration") solution in order to calibrate any desired value within the measurement range. The Autocal control block can include electronics to control the creation and delivery of the mixed calibration solution.

With continuing reference to FIG. 2, the sensor is used to measure glucose in the interstitial or other biological fluids. It can be housed in a cannula or similar tube like structure 42 in order to deliver calibrant to the sensor in situ. The sensor AFE 34 includes electronics to interface to the sensor and can provide bias or stimulus and measure electrical changes in the sensor. The MCU 30 has digital electronics to run the system program and control the overall operation of the system. The Data Interface includes electronics to facilitate the sending and receiving of data between this system and a remote device, and can be either a wired or wireless interface.

In operation, on a periodic basis an automatic calibration sequence will be initiated to perform one or more of the following operations:

Measure the glucose value in the interstitial fluid by measuring the current from the sensor and calculating the glucose value using the most recent calibrated transfer function;

If glucose value is less than 250 mg/dL, bathe the sensor in a high value control solution such as 500 mg/dL. If the glucose value is 250 mg/dL or greater, bathe the sensor in a low value control solution such as 50 mg/dL. After waiting for the sensor to respond, measure the current from the sensor and note associated calibrant value;

Program the control solution or calibrant to be the measured glucose value and bathe the sensor with the solution. After waiting for the sensor to respond, measure the current from the sensor and note associated calibrant value;

Use the known calibrant values and measured currents to calculate the gain and offset in the form of y=mx+b where m is the gain and b is the offset, and store the result; and Wait for the sensor to rid itself of the calibrant and where it is bathed in the interstitial fluid. Measure the glucose value in the interstitial fluid by measuring the current from the sensor and calculating the glucose using the most recent calibrated transfer function. This calibration sequence serves the purpose of performing a two point calibration, which is more accurate than a single point calibration, and it serves as a check on the sensor operation by using a calibrant value far from the current value as the first point, and returns the sensor to normal.

Although various embodiments have been described using specific terms and devices, such description is for illustrative purposes only. The words used are words of description rather than of limitation. It is to be understood that changes and variations may be made by those of ordinary skill in the art without departing from the spirit or the scope of various inventions supported by the written disclosure and the drawings. In addition, it should be understood that aspects of various other embodiments may be interchanged either in whole or in part. It is therefore intended that the claims be interpreted in accordance with the true spirit and scope of the invention without limitation or estoppel.

What is claimed is:

1. A method for in situ calibration of implantable sensors comprising;

providing a first reservoir containing a first calibration solution;

providing a second reservoir containing a second calibration solution different from the first calibration solution;

pumping the first calibration solution with a first electric pump separate from the first reservoir and the second calibration solution with a second electric pump separate from the second reservoir into a mixing valve to provide a third calibration solution having a calibration value that is intermediate to that of the first calibration solution and the second calibration solution due to the mixing of the first calibration solution and the second calibration solution within the mixing valve;

bathing a subcutaneous sensor coupled to an output of the mixing valve with the third calibration solution; and measuring a sensor current of the subcutaneous sensor as it is being bathed in the third calibration solution;

whereby the first electric pump and the second electric pump are coupled to a microcontroller.

2. A method for in situ calibration of implantable sensors as recited in claim 1 further comprising developing a single point calibration transfer function from the measured sensor current and the calibration value.

3. A method for in situ calibration of implantable sensors as recited in claim 2 wherein developing the single point calibration transfer function comprises:

storing the measured sensor current and the calibration value in a memory; and calculating the single point calibration with a processor coupled to the memory.

4. A method for in situ calibration of implantable sensors as recited in claim 3 wherein at least one of the first calibration solution and the second calibration solution is a glucose solution.

5. A method for in situ calibration of implantable sensors as recited in claim 4 further comprising:

measuring a glucose value with the subcutaneous sensor; and developing a calibrated glucose value from the measured glucose value using the single point calibration transfer function.

6. A method for in situ calibration of implantable sensors as recited in claim 5 wherein the calibration value of the third calibration solution is close to the measured glucose value.

7. A method for in situ calibration of implantable sensors as recited in claim 6 wherein the calibration value of the third calibration solution is adjusted by electrically controlling the first electric pump and the second electric pump with the microcontroller to vary the proportion of the first calibration solution and the second calibration solution in the mixing valve.

8. A method for in situ calibration of implantable sensors as recited in claim 1 further comprising:

providing a third reservoir including a cleaning solution; and pumping the cleaning solution with a third electric pump separate from the third reservoir and coupled to the microcontroller to bathe the subcutaneous sensor with the cleaning solution.

9. A method for in situ calibration of implantable sensors comprising;

providing a first reservoir containing a first calibration solution;

providing a second reservoir containing a second calibration solution different from the first calibration solution;

pumping the first calibration solution with a first electric pump separate from the first reservoir and the second calibration solution with a second electric pump separate from the second reservoir into a mixing valve to provide a third calibration solution having a third calibration value that is intermediate to the first calibration solution and the second calibration solution due to the mixing of the first calibration solution and the second calibration solution within the mixing valve;

bathing a subcutaneous sensor coupled to an output of the mixing valve with the third calibration solution;

measuring a first sensor current of the subcutaneous sensor as it is being bathed in the third calibration solution;

pumping the first calibration solution with the first electric pump and the second calibration solution with the second electric pump into the mixing valve to provide a fourth calibration solution having a second calibration value that is intermediate to the first calibration solution and the second calibration solution and different from the third calibration solution;

bathing the subcutaneous sensor with the fourth calibration solution;

measuring a second sensor current of the subcutaneous sensor as it is being bathed in the fourth calibration solution;

whereby the first electric pump and the second electric pump are coupled to a microcontroller.

10. A method for in situ calibration of implantable sensors as recited in claim 9 further comprising developing a two point calibration transfer function from the first sensor current, the first calibration value, the second sensor current, and the second calibration value.

11. A method for in situ calibration of implantable sensors as recited in claim 10 wherein developing the two point calibration transfer function comprises:

storing the first measured sensor current and the first calibration value in non-transitory computer readable media;

storing the second measure sensor current and the second calibration value in non-transitory computer readable media; and calculating the two point calibration transfer function with a processor coupled to the computer readable media.

12. A method for in situ calibration of implantable sensors as recited in claim 11 wherein at least one of the first calibration solution and the second calibration solution is a glucose solution.

13. A method for in situ calibration of implantable sensors as recited in claim 12 further comprising:

measuring a glucose value with the subcutaneous sensor; and developing a calibrated glucose value from the measured glucose value using the two point calibration transfer function.

14. A method for in situ calibration of implantable sensors as recited in claim 13 further comprising calculating the gain (m) and offset (b) for the subcutaneous sensor, whereby a transfer function f(x) for the sensor comprises $y=f(x)=mx+b$.

15. A method for in situ calibration of implantable sensors as recited in claim 14 wherein the second calibration value is closer to the measured glucose value than the first calibration value.

16. A method for in situ calibration of implantable sensors as recited in claim 15 wherein the first calibration value and the second calibration value are adjusted by electrically controlling the first electric pump and the second electric pump with the microcontroller to vary the proportions of the first calibration solution and the second calibration solution in the mixing valve.

17. A method for in situ calibration of implantable sensors as recited in claim 9 further comprising:

providing a third reservoir including a cleaning solution; and pumping the cleaning solution with a third electric pump separate from the third reservoir and coupled to the microcontroller to bathe the subcutaneous sensor with the cleaning solution.

\* \* \* \* \*